(12) United States Patent
Lytle et al.

(10) Patent No.: US 8,486,125 B2
(45) Date of Patent: Jul. 16, 2013

(54) DIABETES SYMPTOM RELIEF THROUGH A LASER BASED MEDICAL DEVICE

(75) Inventors: Larry Lytle, Rapid City, SD (US); Alf-Kare Eide Riisnaes, Rapid City, SD (US); Kip Lytle, Rapid City, SD (US); Shawn Gab, Rapid City, SD (US)

(73) Assignee: 2035, Inc., Rapid City, SD (US)

(*) Notice: Subject to any disclaimer, the term of this patent is extended or adjusted under 35 U.S.C. 154(b) by 604 days.

(21) Appl. No.: 12/717,960

(22) Filed: Mar. 5, 2010

(65) Prior Publication Data
US 2011/0218596 A1    Sep. 8, 2011

(51) Int. Cl.
*A61N 5/06*    (2006.01)
(52) U.S. Cl.
USPC ............................................. 607/89
(58) Field of Classification Search
None
See application file for complete search history.

(56) References Cited

U.S. PATENT DOCUMENTS

2011/0087312 A1*   4/2011   Shanks et al. .................. 607/89
2011/0125229 A1*   5/2011   Lytle et al. ..................... 607/89

* cited by examiner

*Primary Examiner* — Jessica Stultz
*Assistant Examiner* — Tuan Nguyen
(74) *Attorney, Agent, or Firm* — Raj Abhyanker, P.C.

(57) ABSTRACT

Disclosed are several methods, apparatus, and a system for providing diabetic symptom relief through a laser based medical instrument. In one embodiment, a method includes generating a radiation of a laser-light created by a laser diode of a first medical instrument. In addition, the method includes applying a treatment of the radiation to a portion of a body. The method also includes reducing elevated blood glucose and/or glycosylated hemoglobin levels caused by one or more metabolic diseases such as diabetes. The method further includes providing a relief from the secondary complications of elevated blood glucose levels such as blurred vision, etc., when the treatment is complete.

4 Claims, 15 Drawing Sheets

| CONDITION 1502 | LOW-LEVEL LASER TREATMENT 1504 |
|---|---|
| TYPE 1 DIABETES | |
| FREQUENT URINATION | TREATMENT MODE C,F; WAVELENGTH Y NANOMETERS |
| UNUSUAL THIRST | TREATMENT MODE A,F; WAVELENGTH M NANOMETERS |
| EXTREME HUNGER | TREATMENT MODE B; WAVELENGTH C NANOMETERS |
| UNUSUAL WEIGHT LOSS | TREATMENT MODE M; WAVELENGTH E NANOMETERS |
| EXTREME FATIGUE AND IRRITABILITY | TREATMENT MODE P; WAVELENGTH M NANOMETERS |
| OTHERS | TREATMENT MODE N; WAVELENGTH S NANOMETERS |
| TYPE 1 DIABETES* 1506 | LOW-LEVEL LASER TREATMENT 1508 |
| ANY OF THE TYPE 1 SYMPTOMS | TREATMENT MODE C; WAVELENGTH Y NANOMETERS |
| FREQUENT INFECTIONS | TREATMENT MODE Q; WAVELENGTH N NANOMETERS |
| BLURRED VISION | TREATMENT MODE B,F; WAVELENGTH W NANOMETERS |
| CUT/BRUISES THAT ARE SLOW TO HEAL | TREATMENT MODE C,T; WAVELENGTH P NANOMETERS |
| TINGLING/NUMBNESS IN THE HANDS/FEET | TREATMENT MODE M,H; WAVELENGTH Q NANOMETERS |
| RECURRING SKIN, GUM, BLADDER INFECTIONS, OTHERS | TREATMENT MODE P,O; WAVELENGTH K NANOMETERS |

TABLE 1550

FIGURE 15

DIABETES SYMPTOM RELIEF THROUGH A LASER BASED MEDICAL DEVICE

FIELD OF TECHNOLOGY

This disclosure relates generally to the field of medical instruments, and, in one embodiment, to several methods, a system, and apparatus of a laser based medical instrument for providing diabetic symptom relief.

BACKGROUND

Diabetes affects millions of people each year. There are two types of diabetes: type 1 diabetes occurs when the pancreas secretes little or no insulin; type 2 diabetes occurs when the body produces too little insulin or has become resistant to insulin's action. As a result of either insulin deficiency or the body's resistance to insulin, the level of glucose in the bloodstream increases causing hyperglycemia. Left untreated, high blood sugar can lead to secondary complications such as elevated blood glycosylated hemoglobin levels (HbAlc), blurred vision, weakness, double vision, cramps, shortness of breath, abdominal pain, leg pain, blindness, nerve damage (neuropathy) and kidney damage.

Various oral and injectable medications are currently used to manage type 1 and type 2 diabetes. Unfortunately, prolonged use of oral medications and/or insulin injections can have undesirable side-effects. For example, oral medications that increase insulin production include: Januvia, which may cause upper respiratory tract infection, sore throat and headache; and Sitagliptin, which has been associated with severe inflammation of the pancreas. In addition, Sulfonylureas such as Glipizide may cause low blood sugar, nausea and weight gain. Insulin injections are also used to treat severe diabetic conditions. However, long term effects of insulin injection treatment are unpredictable and can lead to further complications in some individuals.

SUMMARY

Disclosed are several methods, apparatus, and a system for providing diabetes symptom relief through a laser based medical instrument. In one aspect, a method includes generating a radiation of a laser-light created by a laser diode of a first medical instrument. In addition, the method includes applying a treatment of the radiation to an application point affected by insulin deficiency or resistance associated with diabetes. The method also includes reducing elevated blood glucose levels (hyperglycemia) caused by either type 1 diabetes or type 2 diabetes. The method further includes providing a relief from secondary complications caused by diabetes, when the treatment is complete. In several embodiments, the medical instrument may be a laser therapy device.

In several embodiments the treatment or therapy administered by the medical instrument to treat a biological medium may be referred to as, but is not limited to, low-level laser therapy (LLLT), laser biostimulation, laser irradiation, laser therapy, low-power laser irradiation, or low-power laser therapy. In several embodiments, the medial instrument may provide laser therapy or laser treatment to the biological medium.

In addition, the method may include adjusting one or more of a pulsation power, a pulsation frequency, and/or a pulsation duration of the radiation to provide the treatment. The wavelength of the radiation may be adjusted by using different laser diodes. The method may include coordinating a delivery of a soliton wave when the radiation of the laser-light is applied. The method may also include coupling the first medical instrument to a second medical instrument. The method may further include generating a first soliton wave through the first medical instrument at a first wavelength and at a first frequency. The method may also include generating a second soliton wave through the second medical instrument at a second wavelength and at a second frequency. In addition, the method may include coordinating a delivery of the first soliton wave and the second soliton wave on a biological medium through an algorithm that controls delivery of laser and diode light of the first medical instrument and the second medical instrument. The method may also include adjusting one or more of the pulsation power, the pulsation frequency, and the pulsation duration of the radiation to provide an additional treatment with a custom mode and/or with a preconfigured mode. The radiation in specific may be provided to one or more application points on a biological medium.

In addition, the method may include authenticating a medical instrument based on an identifier associated with the medical instrument using a processor. The method may include authenticating a user of the medical instrument based on a password using the processor. In addition, the method may include generating a graphical representation of the medical instrument. The method may also include providing a set of rules associated with the medical instrument based on the identifier and the user. The method may further include generating a custom mode of operation of the medical instrument based on a response of the user. The method may also include creating a name associated with the custom mode of operation. In addition, the method may include automatically programming the medical instrument based on the custom mode. The method may also include sharing the custom mode with other users and other medical instruments based on the set of rules and a preference of the user. The disease associated with the hyperglycemia may be diabetes. In addition, the method includes treating a diabetes patient with high blood glucose levels by laser-light radiation, administered every other day for 18-60 day durations.

In addition, the method may include adjusting frequency and pulsation duration of the laser-light radiation to provide a treatment with a preconfigured mode.

In another aspect, the method includes generating a radiation of a laser-light created by a laser diode. In addition, the method includes applying a treatment of the radiation to a portion of a body part. The method also includes reducing a condition that includes reduction in a blood glucose level, a blood glycosylated hemoglobin level (HbAlc), and in turn reducing the secondary complications of diabetes such as blurred vision, weakness, double vision, cramps, shortness of breath, abdominal pain and leg pain. The method further includes providing a relief from the secondary complications when the treatment is complete. In addition, the method may include providing a relief from diabetes.

In yet another aspect, the method includes generating a radiation of a laser-light created by a laser diode. In addition, the method includes monitoring the radiation. The method also includes applying a treatment of the radiation to a portion of a body part. The method further includes reducing hyperglycemia in diabetes. In addition, the method includes providing a relief from the condition when the treatment is complete. The method may also include using a warning Light Emitting Diode (LED) to monitor the radiation.

The methods disclosed herein may be implemented in any means for achieving various aspects, and may be executed in a form of a machine-readable medium embodying a set of instructions that, when executed by a machine, cause the machine to perform any of the operations disclosed herein.

Other features will be apparent from the accompanying drawings and from the detailed description that follows.

BRIEF DESCRIPTION OF THE DRAWINGS

Example embodiments are illustrated by way of example and are not limited to the figures of accompanying drawings, in which like references indicate similar elements and in which:

FIG. 15 shows low-level laser treatment for some of the symptoms exhibited by diabetic type 1 or type 2 patients. The table also shows different modes of treatment with varied wavelength of the low-level laser for treating a particular symptom.

Other features of the present embodiments will be apparent from accompanying drawings and from the detailed description that follows.

DETAILED DESCRIPTION

Example embodiments, as described below, may be used to provide several methods, a system, and apparatus of a laser based medical instrument for reducing hyperglycemia in diabetic patients. Although the present embodiments have been described with reference to specific example embodiments, it will be evident that various modifications and changes may be made to these embodiments without departing from the broader spirit and scope of the various embodiments.

Figure 1:
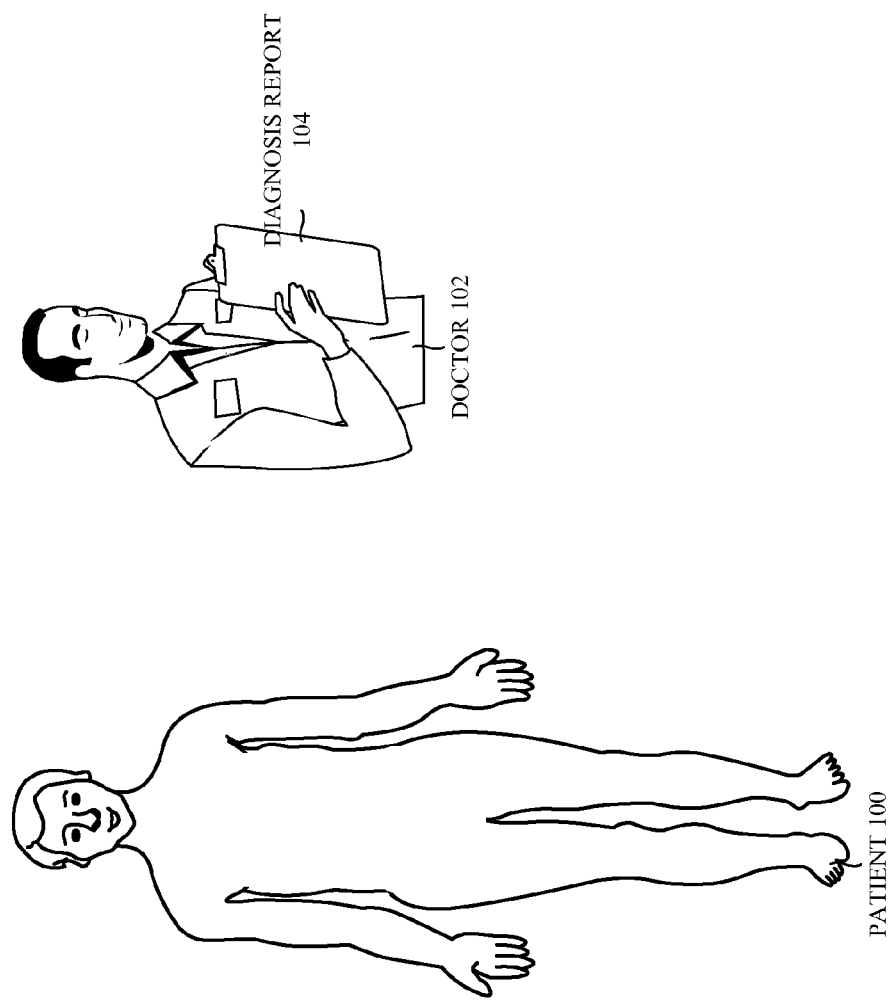
FIG. 1 illustrates a patient and a doctor diagnosing the patient, according to one or more embodiments.

FIG. 1 illustrates a patient 100 and a doctor 102 diagnosing the patient 100, according to one or more embodiments. The patient 100 may be an individual suffering from very high levels of glucose and HbAlc in their blood. In one embodiment, the patient 100 may be suffering from diabetes. Glucose can act as an oxidizing agent in glycation breakdown depending on the composition of surrounding molecules. Glucose reacts non-enzymatically with protein amino groups to initiate glycation, the early stage of the Maillard reaction, leading to crosslinking and browning of the proteins via the formation of advanced glycation end products (AGEs). The AGEs are responsible for various biochemicals in tissues which can lead to development of several complications in diabetes including, but not limited to, neuropathy, angiopathy.

The monocyte macrophage plays an important role in this process both by removing the senescent molecules that have accumulated AGEs over time and by initiating the steps that lead to new protein synthesis and tissue remodeling. By regulating the amounts of active macrophages via laser-light radiation, it is possible to regulate blood glucose and AGE breakdown and prevent development of complications from diabetes. The doctor 102 may diagnose the patient 100 to generate a diagnosis report 104. The diagnosis report 104, inter alia may include blood level of glucose, blood level of glycosylated hemoglobin, blurred vision, weakness, double vision, cramps, shortness of breath, abdominal pain and leg pain in the patient's body. The doctor 102 may use the diagnosis report 104 to determine a type of treatment for the patient 100. In one or more embodiments, the patient 100 may choose a treatment using a set of substantially similar medical instruments described herein.

Figure 2A:
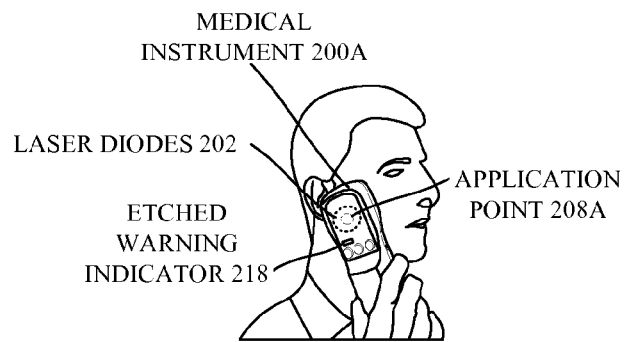
FIG. 2A-C illustrates a treatment being provided to a part of patient body suffering from diabetes, according to an example embodiment.
Figure 2B:
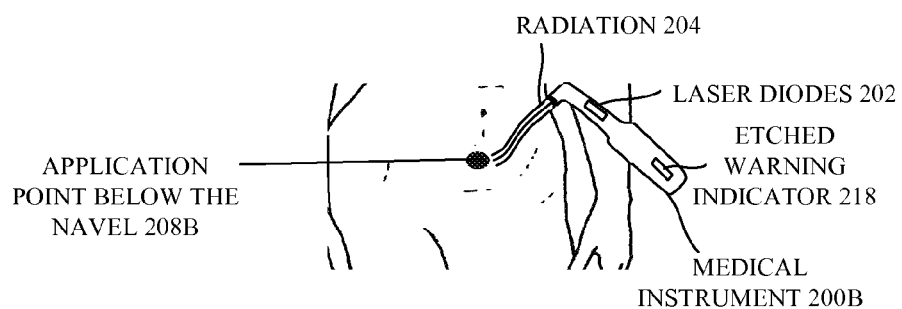
Figure 2C:
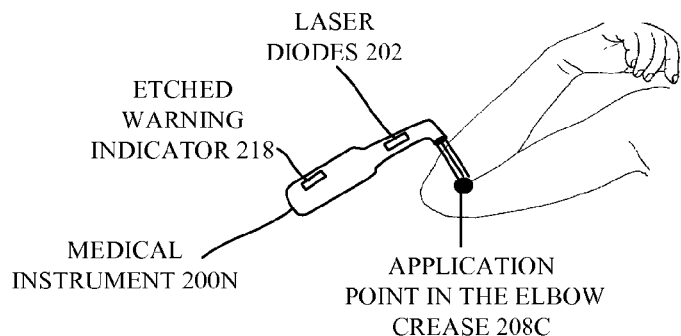

FIG. 2A-C illustrates a treatment being provided to application points for a diabetic patient 100 according to an example embodiment. In particular, FIG. 2A-C illustrates a medical instrument 200A-B, a set of laser diodes 202, a radiation 204, an application point 208A-C, according to one or more embodiments.

In an example embodiment, as described in FIG. 1, the patient 100 may be suffering from diabetes. In one or more embodiments, treatment may be provided by providing radiation to the application point 208A-C using the medical instruments 200A-N. In an example embodiment, FIG. 2A-C illustrates treatment being provided to the affected area 208A-C of the patient's various application points 208. Application points as described herein may include proprioceptive points, acupoints, pressure points and other points. The treatment may be provided by delivering the radiation 204 on the application point 208A-C. The radiation 204 as discussed herein may be an energy that is transmitted in the form of soliton waves. The soliton waves may be a self-reinforcing solitary wave that maintains its shape while traveling at a constant speed. In one or more embodiments, the radiation 204 may be generated from a laser-light generated by the set of laser diodes 202 of the medical instruments 200A-B. The medical instruments 200A-B may generate the soliton waves from the one or more substantially planar laser diode(s) 202. The laser diode(s) 202 may be a semiconductor device(s) that produces coherent radiation in which the waves are all at the same frequency and phase. In one or more embodiments, the laser diodes of the medical instrument 200A-N may be configured to adjust one or more of a pulsation power, a pulsation frequency, and a pulsation duration of the radiation to provide the treatment. In one or more embodiments, the pulsation power, a pulsation frequency, and a pulsation duration of the laser diodes 200 may be adjusted as per requirements. The requirements may vary as per therapeutic condition of a patient.

In one or more embodiments, the radiation 204 may be delivered on areas (e.g., application points) affected by diabetes (e.g., type 2) to reduce blood glucose and HbA1c. The radiation 204 being transmitted in a form of the soliton waves may be generated at a particular frequency. In one or more embodiments, the pulsation frequency and the pulsation duration of the radiation 204 may be adjusted to provide treatment based on requirements and condition of the patient 100. In one or more embodiments, the pulsation frequency and the pulsation duration of the radiation 204 may be adjusted based on a custom mode. In one or more embodiments, the medical instrument 200A-B may be configured to generate a radiation at a wavelength of approximately ~660 nm or ~808 nm. In yet another embodiment, the medical instrument 200A-B may be configured to generate radiation with several wavelengths between 480 nm to 940 nm. In one or more embodiments, delivery of soliton waves may be coordinated when the radiation 204 of the laser-light is applied.

In an example embodiment, FIG. 2A illustrates providing treatment to the application point area 208A in front of the left ear over the TMJ of the patient 100. FIG. 2B illustrates delivering the radiation 204 on the affected area 208B of the application point. The medical instrument 200A-B may generate the radiation 204 to be delivered to an application point located in the 208A. FIG. 2B illustrates delivery of the radiation 204 to an application point located just below the navel point 208B. FIG. 2C illustrates delivery of the radiation 204 to an application point located in an elbow crease 208C. The delivery of the radiation 204 to the application point may be for a specific duration of time and for a suggested course. For example, the treatment for diabetes type 2 may be for one minute, repeated three times. In one or more embodiments, the duration of the treatment (providing radiation) may be pre-determined based on a mode or based on the suggestion provided by the doctor 102. In one or more embodiments, the medical instrument 200A-B (or other medical instruments 200A-N) may be configured to radiate for a specific duration (and specified number of times or cycles) for a specific treatment based on a medical condition. Delivering the radiation 204 may reduce high blood glucose levels in a diabetic patient. Relief may be obtained after reduction of blood glucose levels when the treatment process is completed (e.g., when the delivery of the radiation 204 for specific period is completed).

FIG. 2A-C illustrates delivery of the radiation 204 by the medical instrument 200A-B on the application point of the patient's body parts 208, according to an example embodiment. In one or more embodiments, the medical instrument 200A-B may optionally include an etched warning indicator 218. In one or more embodiments, the etched warning indicator 218 may be used to monitor the radiation 204. When the instrument is emitting radiation the etched warning indicator 218 may illuminate. The etched warning indicator 218 may emit light for a duration suggested for the treatment, thereby indicating a user to use the medical instrument 200A-B on the application points for the suggested amount of time.

It has to be noted that the etched warning indicator 218 may emit light up to a certain amount of time for which the etched warning indicator 218 is configured for the duration of the treatment. In one embodiment, once the duration of treatment elapses, the etched warning indicator 218 stops emitting light and the medical instrument 200A-B stops emitting radiation.

Figure 3C:
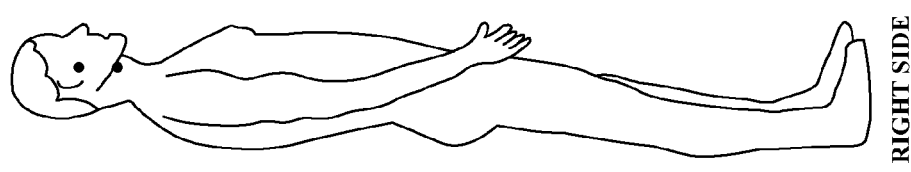
FIG. 3A-C illustrates several application points in a human body for treating diabetes.
Figure 3B:
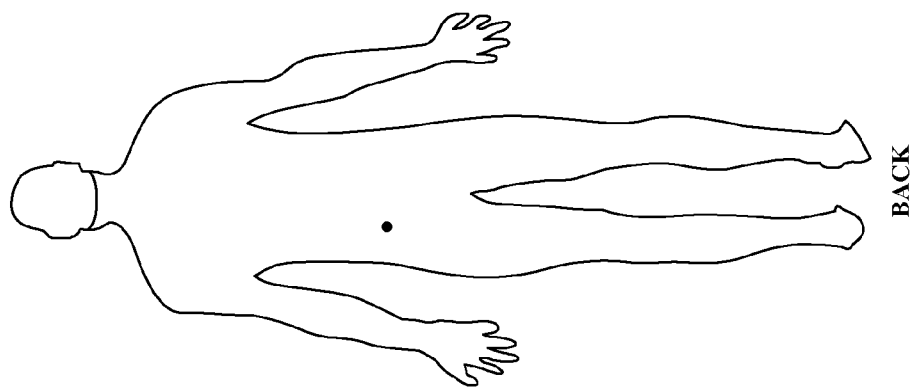
Figure 3A:
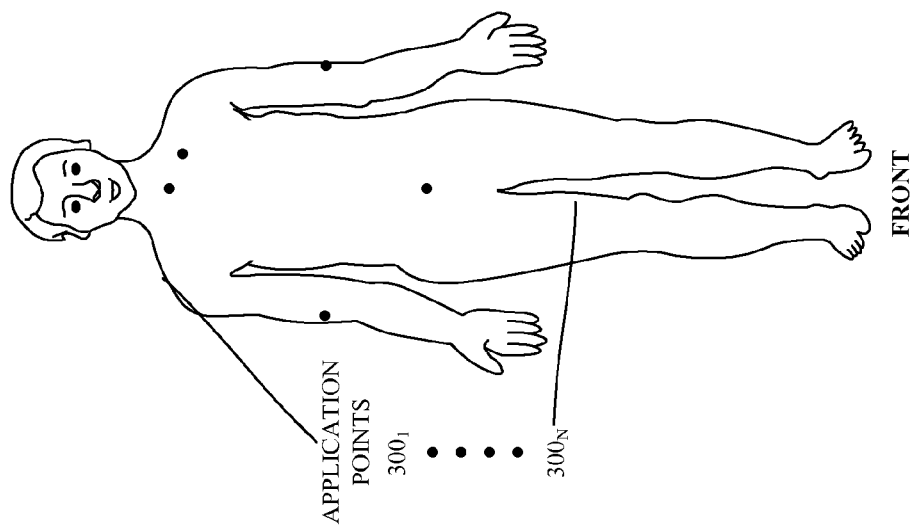

FIG. 3A-C illustrates several application points on a human body. The application points 300$_{1-N}$ are illustrated in FIG. 3A-C. For the diabetic patient, the points as outlined in the figures may be within the following locations: just in front of the left ear over the TMJ; under the angle of the jaw with the laser pointed upwards at a 45 degree angle; two finger widths below the collar bone and three finger widths from the arm pit; over the neck below the Adams apple, over the "V" where the collar bones meet; over the left kidney in the small of the back approximately one hand width above the belt and one hand width to the left of the spine; and a spot hand width below and in line with the navel and extreme edge of the elbow crease. Treatment may be applied to various application points in the body.

The brain derives much of its feedback information from a process called proprioception. The proprioception is a stimulation of a body tissue to activate protective mechanisms. There are other points such as acupuncture points (also called as acupoints) which are located across anatomy that affect a specific organ. Application points as described herein may include proprioceptive points, acupoints, pressure points and other points that may be used as treatment points using the medical instruments. By activating the application points with the medical instrument (e.g., Q1000® by 2035, Inc.™), the body responds through its voluntary nervous/muscular system, but in an involuntary way. The Central Nervous System is a network of nerve fibers that extend everywhere throughout the human body. These nerve fibers send signals to the organs and muscles, and the nerves and muscles responds to these signals by sending response signals back to the brain. All of this signaling occurs automatically and is not under an individual's conscious control. When the laser (e.g., Q1000® by 2035, Inc.™) is applied to these application points for approximately one minute, these muscles release and the application signal to the brain changes, which in turn positively affects the Sympathetic and Parasympathetic divisions of the Autonomic Nervous System. Releasing the Sympathetic division controls stress and subsequently the organ functions improve and the pancreatic function may improve the production of insulin.

Proprioception may be defined as the unconscious perception of movement spatial orientation arising from stimuli within the body itself. It is also the body's way of protecting itself. Proprioception directly affects the autonomic nervous system. The autonomic nervous system regulates organ function by coordinating sympathetic and parasympathetic signals. When the sympathetic nervous system is stimulated, there may be increased body activity, increased stress, increased blood pressure, increased heart rate and increased breathing rate. When these areas increase, there may be a simultaneous decrease of glandular, stomach and intestinal function. The body becomes more acidic, goes into a state of oxidation, stress may be increased, and disease may be eminent. If activity in the parasympathetic nervous system increases by stimulation of the body's application points, the opposite happens. The heart and breathing rates slow, blood pressure and acid levels normalize, there may be an increase in the glandular and gut activity, the body reserves increase, and there may be less disease. By balancing the sympathetic and parasympathetic nervous systems there may be less disease.

Instrument

Figure 4:
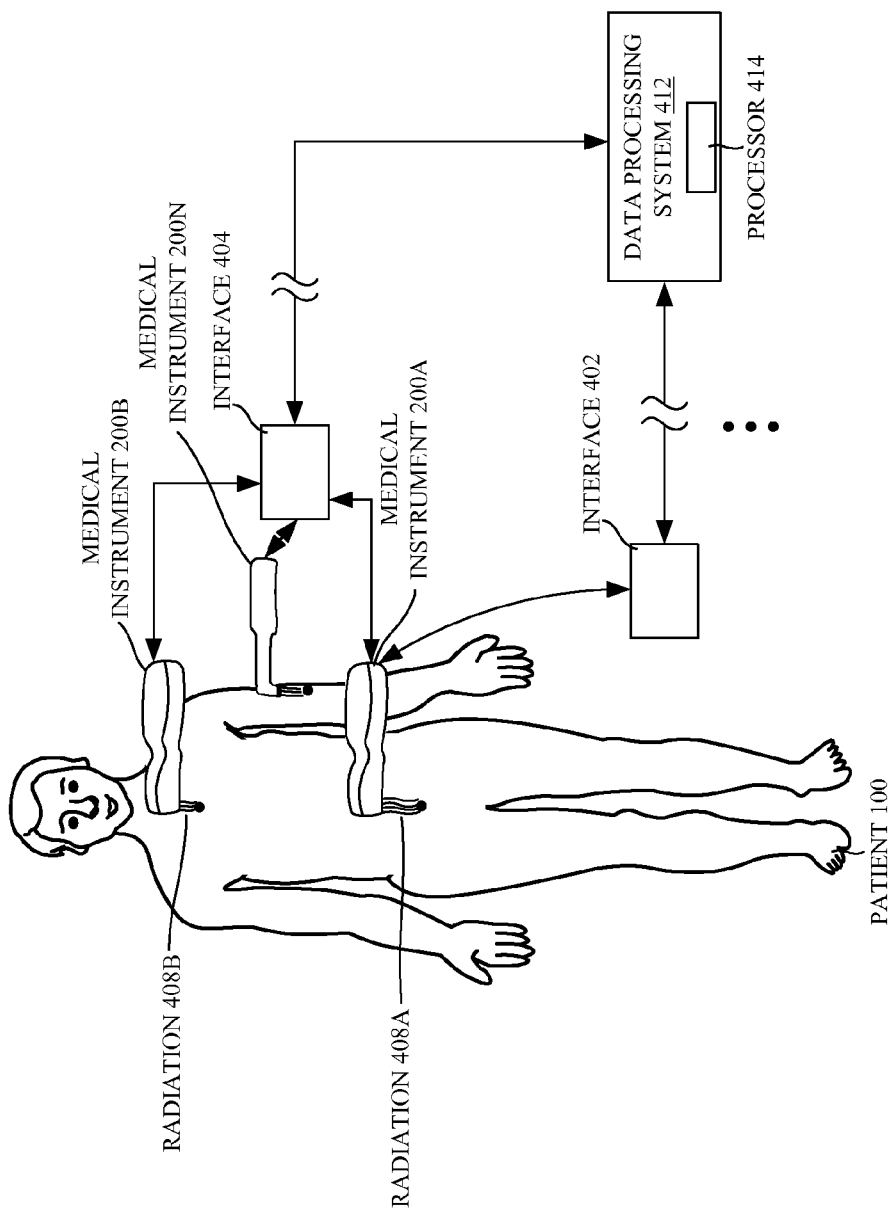
FIG. 4 illustrates a system view that illustrates medical instruments being communicatively coupled and coordinated through a data processing system for treatment of the patient, according to an example embodiment.

FIG. 4 is a system view that illustrates medical instruments 200A-N being communicatively coupled and coordinated through a data processing system 412 for treatment of the patient 100, according to an example embodiment. In particular, FIG. 4 illustrates the medical instruments 200A-N, interfaces 402-404, radiations 408A-N, the data processing system 412, a processor 414, and the patient 100, according to one embodiment.

In one or more embodiments, the medical instruments 200A-N may not be coupled to the data processing system during treatment. In one or more embodiments, the medical instruments 200A-N described herein are portable and handheld devices. The medical instruments 200A-N may be communicatively coupled to each other and to the data processing system 412 through the interface(s) 402-404. The interface(s) 402-404 may serve as a communication link between the medical instruments 200A-N. In one or more embodiments, there may be any number of interfaces to enable coupling of medical instruments 200A-N. The aforementioned data processing system 412 may be a computing device (e.g., computer) that includes the processor 414. In one or more embodiments, the data processing system 412 may be used for communicating mode information to the medical instruments 200A-N through the interfaces 402-404.

In one or more embodiments, the medical instruments 200A-N coupled to each other through the interfaces 402-404 may generate the radiations 408A-N individually or in coordination. In one or more embodiments, the radiation 408A-N (soliton waves) may be generated from the laser-light generated by the laser diodes of the medical instruments 200A-N. In one or more embodiments, the radiations 408A-N may be generated in combination and coordination or individually. In another embodiment, an algorithm that coordinates the delivery of laser-light may be controlled by the medical instruments 200A-N. The algorithm may be designed based on the requirement of a medical procedure. It should be noted that the delivery of the radiations is possible even without coordination.

In an example embodiment, each of the medical instruments 200A-N may generate the radiations 408A-N at preconfigured modes. In one or more embodiments, each of the medical instruments 200A-N may be configured individually to generate the radiations 408A-N at specified frequencies. In one or more embodiments, medical instruments 200A-N may be communicatively coupled to the data processing system 412 to communicate new modes to the medical instruments 200A-N. The data processing system 412 may communicate new modes to the medical instruments 200A-N.

There may be a variety of operational modes for operating the medical instruments 200A-N. The operational modes may be based on a suggested form of a treatment. In one or more embodiments, the medical instruments 200A-N may coordinate among each other synchronously, asynchronously, or in a pattern to provide laser therapy. The radiations 408A-N generated may be delivered on biological mediums (e.g., application points in a human body) based on a procedure of medical treatments. In another embodiment, the medical instrument 200A may be used by a patient for treatment.

In an example embodiment, the radiations 408A-N may be generated by canceling a nonlinear effect and a dispersive effect in a region between an emitting region of the medical instrument 200A-N and the biological medium. The dispersive effect may be a dispersion relationship (e.g., variation of wave propagation with wavelength or frequency of a wave) between a frequency and a speed of the soliton wave. In one or more embodiments, the medical instruments 200A-N may include primary device and probe devices. The primary device (e.g., the medical instrument 200A) is explained in FIG. 5. The medical instrument 200B may be explained in detail in FIG. 11.

Figure 5:
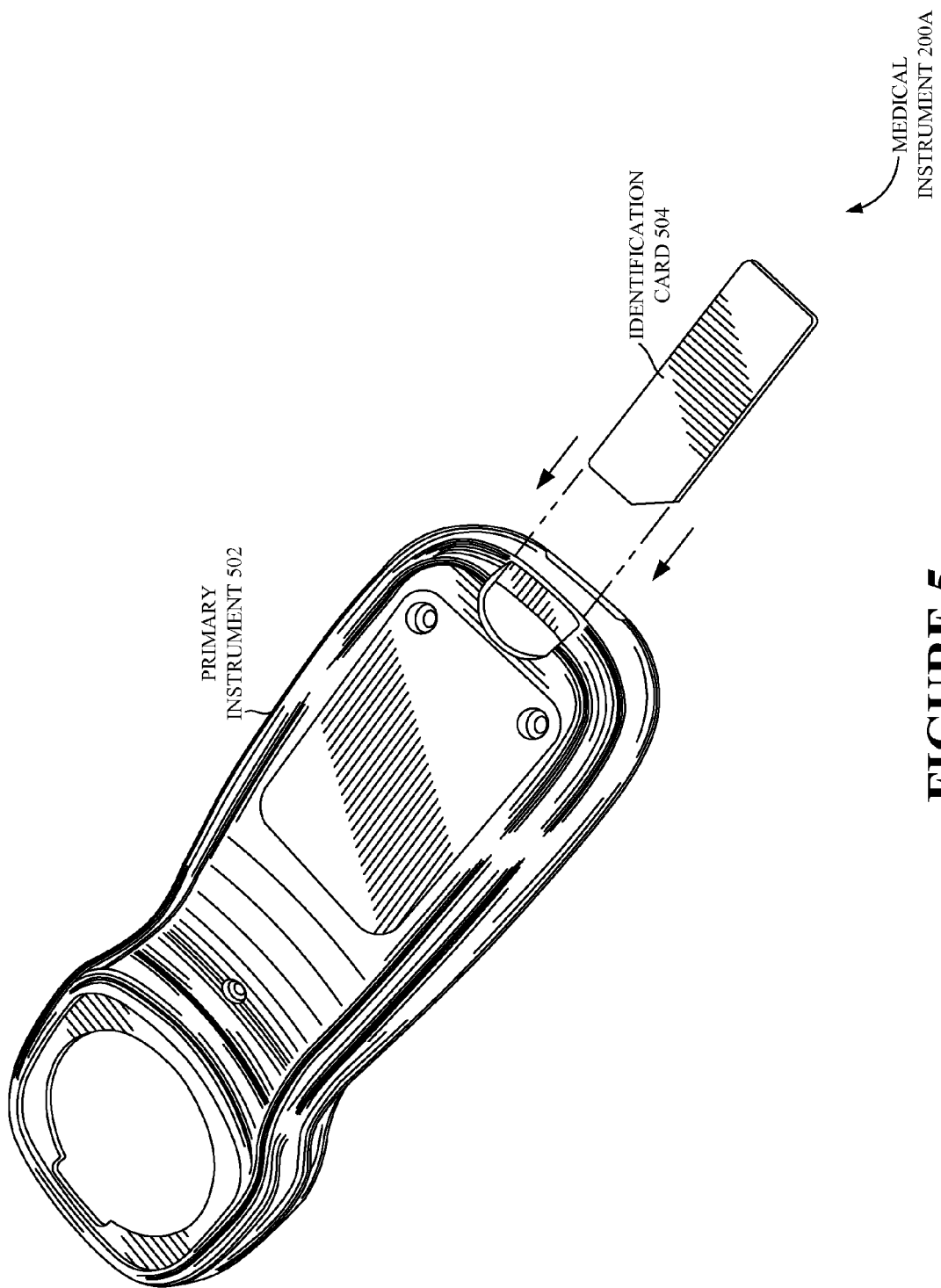
FIG. 5 illustrates a schematic view of a primary instrument, according to one embodiment.

FIG. 5 is a schematic view of a primary instrument 502, according to one embodiment. In particular, FIG. 5 illustrates the primary instrument 502 and an identification card 504, according to one embodiment. In one or more embodiments, the identification card 504 may be used as the mode card, where the modes can be stored on the medical instrument 200A. The identification card 504 may activate the modes stored on the medical instrument 200A.

In an example embodiment, the medical instrument 200A may be the primary instrument 502. The primary instrument 502 as described herein may include the identification card 504.

In one or more embodiments, the identification card 504 of the medical instrument 200A may be used for selecting an operational mode of the medical instrument 200A. The identification card 504 coupled to the primary instrument 502 may be removable by a user of the medical instrument 200A. The operational modes may be associated with a suggested form of a medical treatment. There may be a variety of operational modes for a treating of a particular ailment. A patient 100 may choose a best mode of treatment based on his condition of the disease. The patient 100 may choose a best operational mode for the treatment using the medical instrument 200A.

In one or more embodiments, the operational modes may be stored on medical instrument 200A, and the best operational mode may be activated by the identification card 504. The identification card 504 may be programmed using an appropriate device. Furthermore, the identification card 504 may be reprogrammed based on a prescription associated with the therapeutic condition of the patient 100. In one or more embodiments, the patient 100 may decide on a custom mode for providing an additional treatment by the medical instrument. In one or more embodiments, a custom mode of operation of the medical instruments 200A-N may be generated and/or determined based on a response of the user. The custom mode that may be suggested by the instrument maker and may be programmed into the identification card 504. The identification card 504 may be communicatively coupled to the primary instrument 502 through a port designated for that purpose. The primary instrument 502 may then generate a radiation based on the mode that is loaded from the identification card 504. In one or more embodiments, a name associated with the custom mode of operation may be created and the configuration associated with the custom mode may be stored in the data processing system 412 for future treatments.

In alternate embodiments, the identification card 504 may be made specific to one therapeutic condition (e.g., diabetes). In one or more embodiments, the operational modes of the medical instruments 200A-N may be provided from the data processing system 412 thereof. In one or more embodiments, the custom mode may be shared with the other medical instruments based on a set of rules and preferences of the user and/or the doctor 102. In one or more embodiments, the custom mode may be shared by communicating the custom mode to the data processing system 412 and applying the custom mode to the other medical instruments through the data processing system 412.

In one or more embodiments, the medical instrument 200A may be used for treatment in general conditions. In one or more embodiments, where there is a requirement of directed, high-power dosage in a narrow region of a biological medium, the second medical instrument 200B, for example, may be a probe device. The probe device may be explained in detail in FIG. 11. The primary device or the medical instrument 200A may be explained in detail in FIG. 10.

Figure 6:
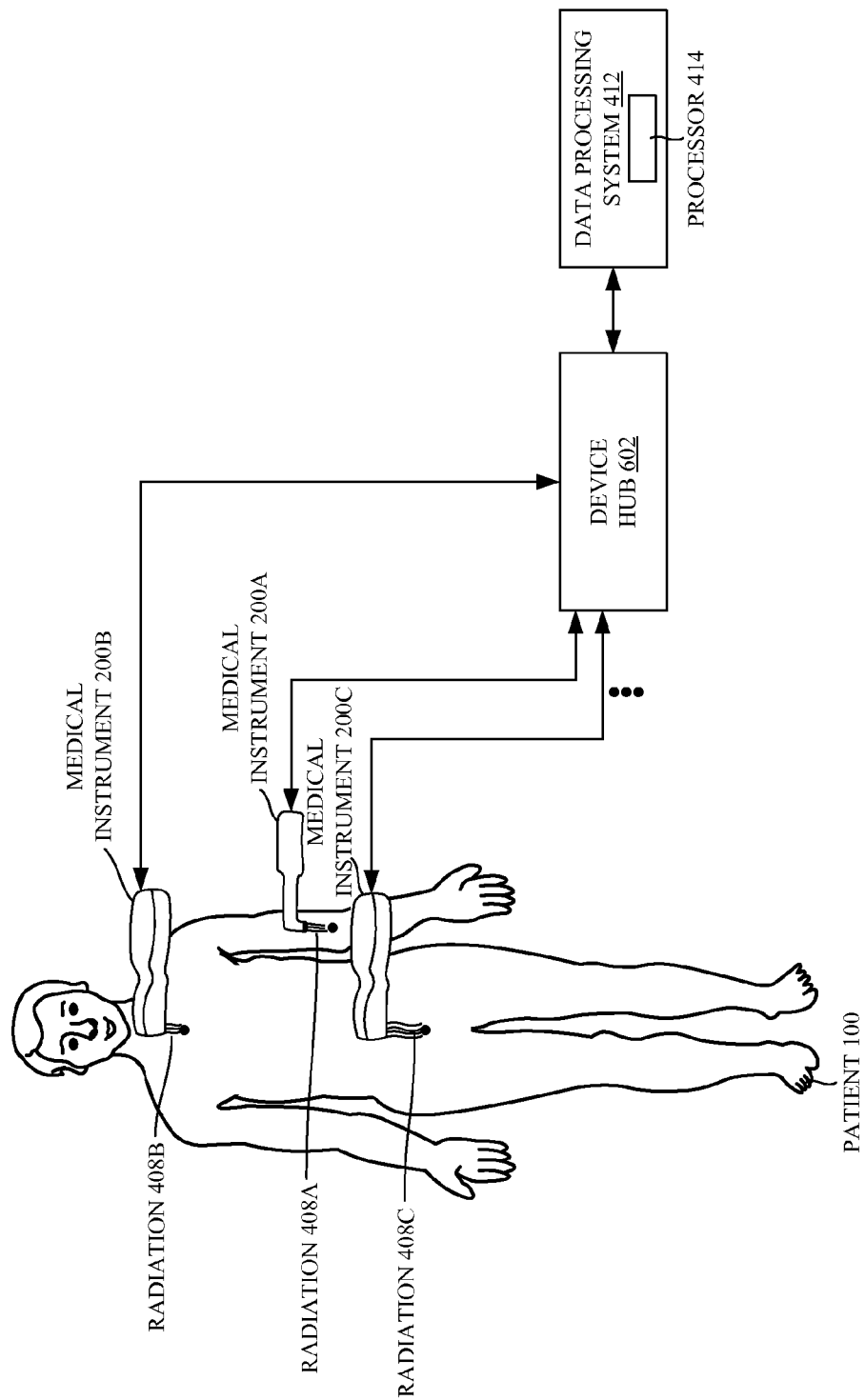
FIG. 6 illustrates an alternative system comprising the medical instruments that are communicatively coupled and coordinated through a data processing system for treatment of the patient, according to another embodiment.

FIG. 6 is an alternative system comprising the medical instruments 200A-N that are communicatively coupled and coordinated through the data processing system 412 for treatment of a patient 100, according to another embodiment. In particular, FIG. 6 illustrates the patient 100, the medical instruments 200A-N, a device hub 602, the radiations 408A-N, the data processing system 412, and the processor 414, according to an alternate embodiment.

FIG. 6 provides an alternative embodiment to the system illustrated in FIG. 4. In an embodiment, the medical instruments 200A-N may be communicatively coupled to the data processing system 412 through the device hub 602. The device hub 602 may be a device that is used to connect the medical instruments 200A-N to the data processing system 412. In an example embodiment, the device hub 602 may serve as a bridge between the medical instruments 200A-N and the data processing system 412. Each of the medical instrument 200A-N may be connected to the device hub 602. The processor 414 in the data processing system 412 may provide modes of treatment to the medical instruments 200A-N through the device hub 602. In one or more embodiments, the system as illustrates in the FIG. 6 may function the same as described in FIG. 4.

Figure 7:
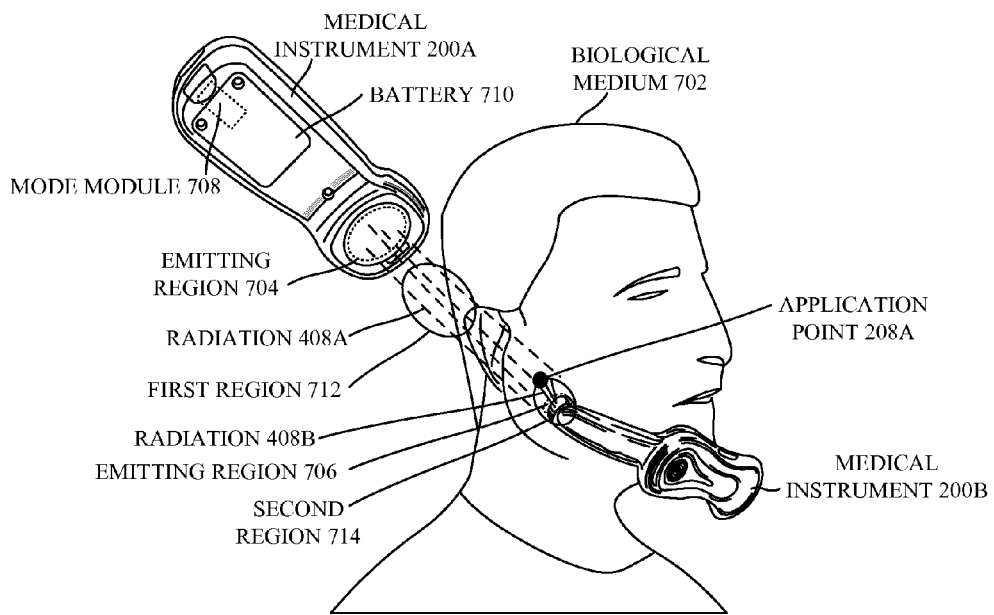
FIG. 7 illustrates a use of the medical instruments used for providing treatment to a biological medium, according to one embodiment.

FIG. 7 is a schematic view illustrating a use of the medical instruments 200A-B for providing treatment to an application point, according to one embodiment. In particular, FIG. 7 illustrates the biological medium 702, an emitting region 704, an emitting region 706, a mode module 708, and a battery 710, according to one or more embodiments.

In an example embodiment, the radiation 408A may be generated by canceling a nonlinear effect and a dispersive effect in a first region 712 between an emitting region of the medical instrument 200A and the biological medium. In an example embodiment, the radiation 408B may be generated by canceling a nonlinear effect and a dispersive effect in a second region 714 between an emitting region of the medical instrument 200B and the biological medium. The dispersive effect may be a dispersion relationship (e.g., variation of wave propagation with wavelength or frequency of a wave) between a frequency and a speed of the soliton wave.

In an example embodiment, the biological medium 702 described herein may be a part of a patient's body such as an application point. In alternate embodiments, the biological medium 702 may be an animal or bird or any other concerned life form affected by the disease. The medical instruments 200A-B described herein may be used on the biological medium 702 individually or in coordination to provide a radiation to the affected areas. The emitting region 704 of the medical instrument 200A may include a set of laser diodes 202 carefully placed and supported by the associated circuitry to generate a radiation. Similarly, the emitting region 706 of the medical instrument 200B may include a laser diode(s) to generate a radiation.

The medical instrument 200A may be powered using the battery 710. In an alternate embodiment, the medical instrument 200A may also be powered through external sources (e.g., through a power cord). In an example embodiment, the battery 710 may be a lithium-ion rechargeable battery to power the medical instruments 200A. In one or more embodiments, a battery charger may be used to charge the battery 710 of the medical instrument 200A. In one or more embodiments, the battery charging capability may be provided through an external connector that may serve purposes not limited to battery charging. A power regulator of the battery 710 (not shown in the figure) may be used to provide stable and accurate power output to the medical instruments 200A-B. In one or more embodiments, the power regulator may closely monitor charge current as well as maximum allowed voltage. In one or more embodiments, the power regulator may prevent over-charging/over-discharging of the battery 710. The mode module 708 may enable the circuitry of the medical instrument 200A to generate a radiation based on a particular operational mode that is loaded into the medical instrument 200A-B through the identification card 504. In one or more embodiments, the medical instruments 200A-N may operate at a power level of approximately ~50 mW or ~500 mW. In yet another embodiment the medical instruments 200A-N may use several laser diodes operating at power levels of approximately ~5 mW.

The medical instrument 200A-N described herein may be authenticated based on an identifier associated with the medical instruments 200A-N using the processor 414. In one or more embodiments, the authentication of the user of the medical instruments 200A-N may be based on a password using the processor 414. In one or more embodiments, a set of rules associated with the medical instrument(s) may be provided based on the identifier and the user.

TABLE 1

Effect of using laser based medical instrument treatment on blood glucose levels in Type 2 Diabetic patients:

| Patient Number | Age | Type of Diabetes | Treatment duration | Medication | Starting blood Glucose level | After Treatment Blood Glucose level |
|---|---|---|---|---|---|---|
| 1 | 76 years | Type 2 | 60 days | Oral hypoglycemic drug | Over 250 mg/dL | 121 mg/dL |
| 2 | 70 years | Type 2 | 60 days | Prednisone | 260 mg/dL | 120 mg/dL |
| 3. | 58 years | Type 2 | 45 days | Oral hypoglycemic medication | 220 mg/dL | 110 mg/dL |

Table 1 shows clinical trials result in reduction of blood glucose levels in type 2 diabetic patients with various treatment periods ranging from 45-60 days. The treatment with a laser based medical device was done along with suggested oral medications. None of the medications were discontinued during the treatment period. Significant drops in blood glucose levels were observed after set period of treatment days.

TABLE 2

Effect of using laser based medical instrument treatment on usage of units of insulin requirement levels in Type 1 Diabetic patient:

| Patient number | Age | Type of Diabetes | Units of Insulin required before treatment | Units of Insulin required after treatment |
|---|---|---|---|---|
| 1. | 15 years | Type 1 | 22 | 2 |

Table 2 shows the beneficial effects of using a laser based medical instrument, reducing the required number of insulin injections from 22 units to 2 units per day in a 15 year old patient having type 1 diabetes for 18 days. The suggested medication was not discontinued during the laser based medical instrument treatment.

Figure 8:
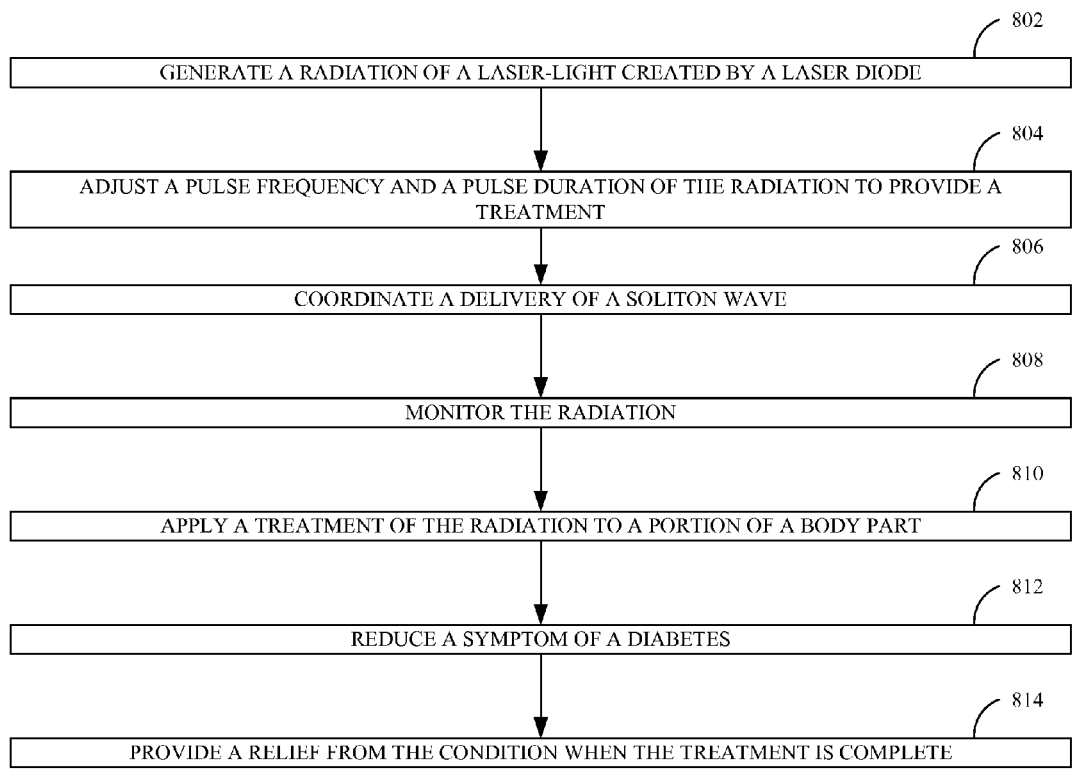
FIG. 8 is a process flow illustrating a treatment being provided through the medical instruments, according to one or more embodiments.

FIG. 8 is a process flow illustrating a treatment being provided through the medical instruments 200A-N, according to one or more embodiments. In operation 802, the radiation 204 of a laser-light created by the laser diodes 202 may be generated. In operation 804, a pulsation frequency and/or a pulsation duration of the radiation 204 may be adjusted to provide a treatment. The wavelength of the radiation may be adjusted by using different laser diodes. In one or more embodiments, the pulsation frequency, the pulsation power, and/or the pulsation duration of the radiation 204 may be also be adjusted to provide a treatment with a custom mode. In operation 806, a delivery of a soliton wave may be coordinated. In operation 808, the radiation 204 may be monitored. In one or more embodiments, the etched warning indicator 218 may be used to monitor the radiation 204. In operation 810, a treatment of the radiation 204 may be applied to a portion of a body part (e.g., as illustrated in FIG. 3). In operation 812, elevated glucose level in the blood may be reduced. In operation 814, a relief from the condition may be provided when the treatment is complete. The first region 712 may illustrate the radiation area of the medical instrument 200A (e.g., as illustrated in FIG. 7). The second region 714 may illustrate the radiation area of the medical instrument 200B (e.g., as illustrated in FIG. 7).

Figure 12:
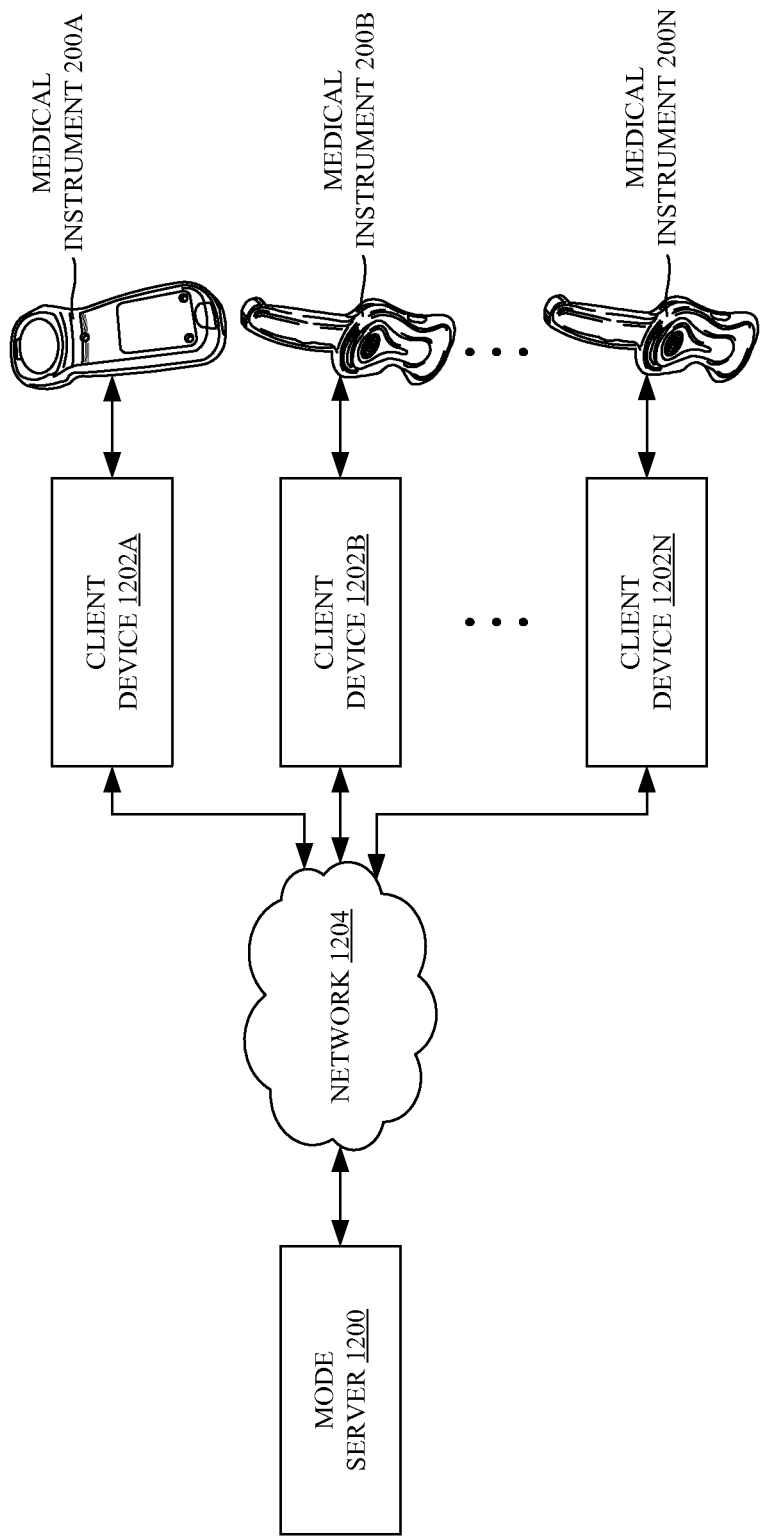
FIG. 12 is a system view illustrating a mode server communicating information associated with a mode to a medical instrument(s) through a client device(s) via a network, according to one or more embodiments.

The treatments described herein may be provided to the patient 100 for reducing hyperglycemia caused due to ailments such as diabetes. The aforementioned treatments may reduce the HbA1c. In addition, the aforementioned treatments may provide a relief from diabetes. Also, in one or more embodiments, operational modes may be provided to the medical instrument over a network as illustrated in FIG. 12. In addition, the modes, information, etc., may also be exchanged over an online social community as illustrated in an example embodiment in FIG. 13.

Figure 9:
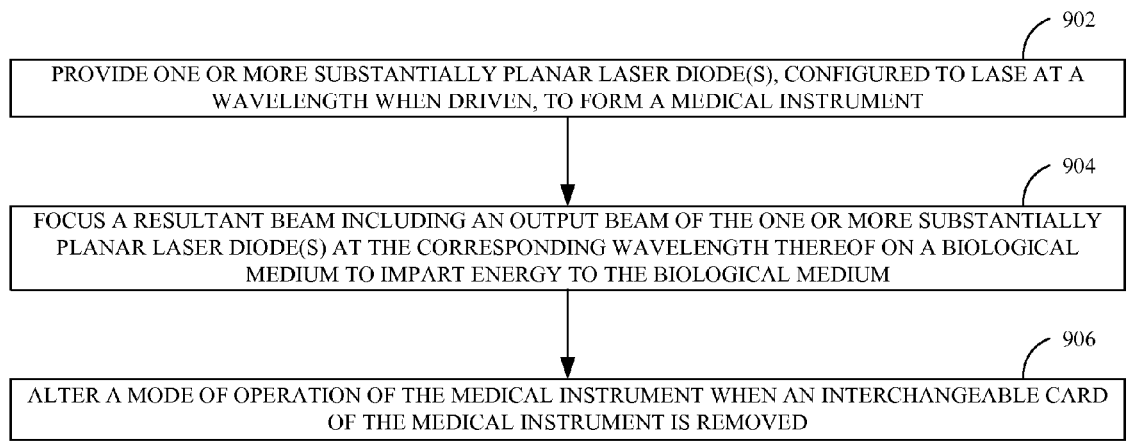
FIG. 9 is a process flow detailing the operations involved in a method of laser therapy, according to one or more embodiments.

FIG. 9 is a process flow detailing the operations involved in a method of laser therapy, according to one or more embodiments. In operation 902, one or more substantially planar laser diode(s), each configured to lase at a wavelength when driven, may be provided to form a medical instrument. In one or more embodiments, a number of substantially planar laser diodes may be arranged in a pre-determined configuration to form a substantially planar laser diode array. In one or more embodiments, the substantial planarity, along with a symmetrical pre-determined configuration, may provide for a symmetrical combination of the output beams from the number of substantially planar laser diodes to form a highly directed resultant beam.

In one or more embodiments, the soliton waves may be generated from the one or more substantially planar laser diode(s). In one or more embodiments, end minors of the one or more substantially planar laser diode(s) may be replaced with anti-reflection coatings, and when the one or more substantially planar laser diode(s) are driven, the optical field evolution in the laser diode(s) may be modeled by using two coupled differential equations (example Equations 1 and 2) as:

$$\frac{\partial \varphi}{\partial z} = i \frac{\partial^2 \varphi}{2 \partial x^2} + (-ihN + (N-1) - \alpha)\varphi, \quad (1)$$

$$D \frac{\partial^2 N}{\partial x^2} = -\pi + N + BN^2 + CN^2 + (N-1)|\varphi|^2, \quad (2)$$

where φ may be the optical field solution, $i=\sqrt{-1}$, x and z the spatial coordinates, h the Henry factor, α the internal loss, N the normalized carrier density $$\left(N = \frac{N'}{N'_{tr}},\right.$$

N' being the carrier density, $N'_{tr}$ and being the transparency carrier density), D the carrier diffusion coefficient, π the current pumping coefficient, B the spontaneous recombination coefficient, and C the Auger recombination rate. Here, a linear dependence of the induced refractive index and gain on the carrier density N' may be assumed.

In one or more embodiments, neglecting carrier diffusion in the z direction, and assuming small diffusion, B=0, and C=0, a generalized complex Ginzburg-Landau equation may be obtained from Equations 1 and 2 as example Equation 3:

$$\frac{\partial \varphi}{\partial z} = i\left(\frac{1}{2} - i\beta\right)\frac{\partial^2 \varphi}{\partial x^2} + \left(\frac{\pi - 1}{1 + |\varphi|^2}(-ih+1) - ih\right)\varphi - \alpha\varphi, \quad (3)$$

where β may account for the transverse carrier diffusion.

In one or more embodiments, soliton wave solutions of the form $\varphi(x)e^{i\lambda z}$ may be numerically obtained. In one or more embodiments, depending on the arrangement of the number of substantially planar laser diodes, constructive interference of the outputs of the number of substantially planar laser diodes may lead to a resultant soliton wave of high amplitude. In one or more embodiments, the resultant soliton wave output may have an amplitude several times higher than a non-soliton wave resultant beam.

In operation 904, the resultant beam may be directed on a biological medium to impart energy to the biological medium (e.g., humans). In one or more embodiments, the resultant beam may be directed on a portion of the human body to treat conditions such as diabetes. In one or more embodiments, in operation 906, a mode of operation of the medical instrument may be altered upon removal of the identification card 504 of the medical instrument. In one or more embodiments, the identification card 504 may be therapeutic condition specific (e.g., diabetes), and the insertion of a new identification card into the medical instrument may result in the medical instrument operating solely in modes of operation specific to the therapeutic condition. In other words, access to mode information is restricted to modes of operation specific to the therapeutic condition.

In one or more embodiments, altering the mode of operation of the medical instrument upon removal of the identification card, as in operation 906, may involve substituting an identification card with another identification card. In one or more embodiments, one identification card may be specific to one therapeutic condition (e.g., diabetes), and the other identification card may be specific to another therapeutic condition (e.g., diabetes).

In one or more embodiments, a mode of operation may include one or more segments, where a segment includes a time of pulsation of the one or more substantially planar laser diode(s) and a frequency of pulsation of the one or more substantially planar laser diode(s). For example, one segment may include pulsing a laser diode at 50 Hz for 20 seconds, and another segment may include pulsing a laser diode at 10 Hz for 30 seconds. In one embodiment, a mode may consist of up to 250 different segments.

Figure 10:
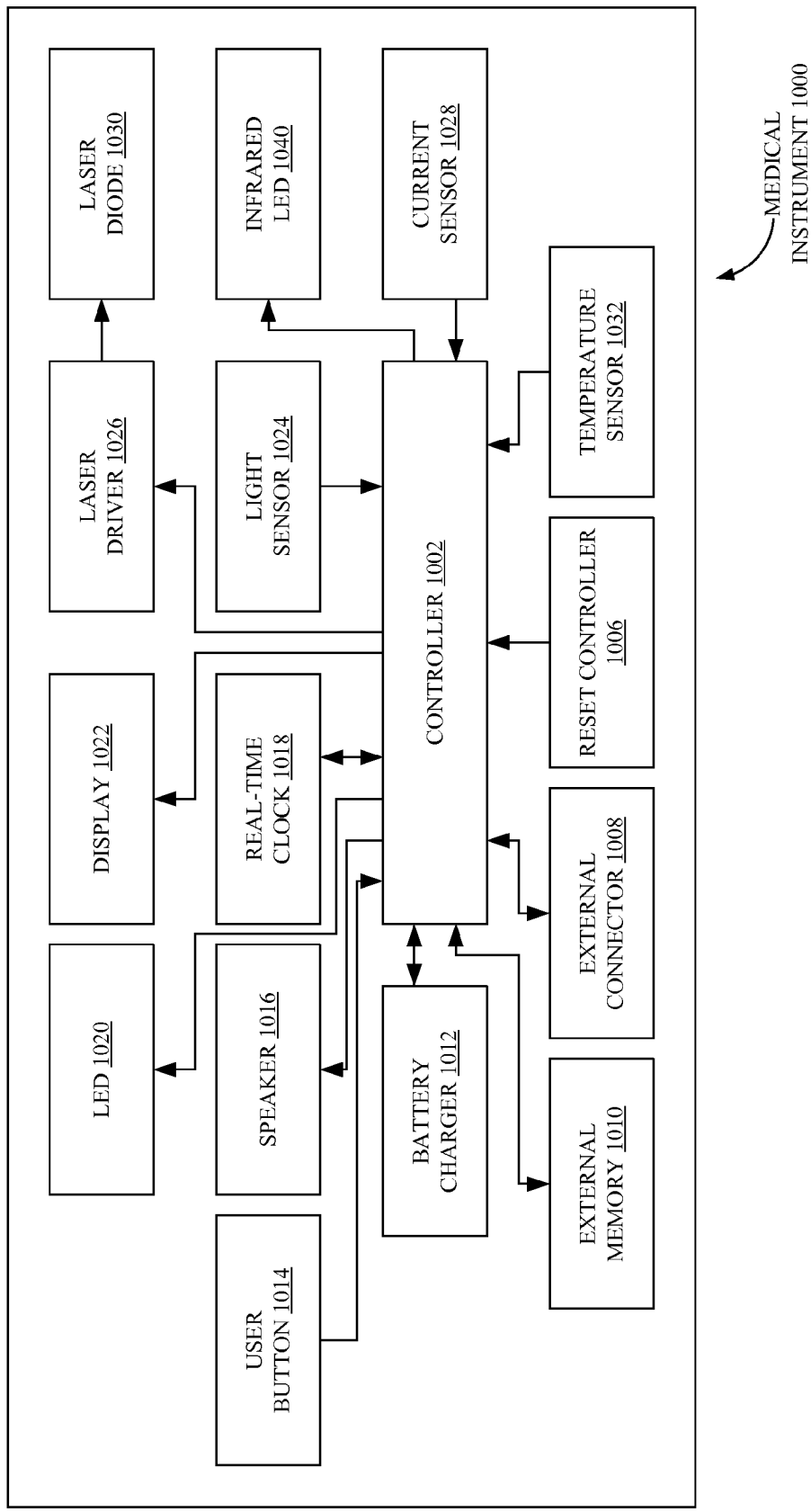
FIG. 10 is a schematic view of a medical instrument, according to one or more embodiments.

FIG. 10 is a schematic view of a medical instrument 1000, according to one or more embodiments. The medical instrument 1000 may in specific describe a schematic representation of the medical instrument 200A and the primary instrument 502. In one or more embodiments, the medical instrument 1000 may include a controller 1002 to control operations fundamental to the working of the medical instrument 1000. In one or more embodiments, the controller 1002 may include a permanent memory (e.g., flash memory) to store firmware associated with controlling the medical instrument 1000. In one or more embodiments, modes of operation may internally be set in the firmware. In one or more embodiments, the controller 1002 is interfaced with a battery charger 1012 to charge a battery (e.g., internal battery) of the medical instrument 1000. In one or more embodiments, the battery charging capability may be provided through an external connector 1008 that may serve purposes not limited to battery charging.

In one or more embodiments, the external connector 1008 may be a multi-pin and multi-use external connector that may also be used to program the internal controller of the medical instrument 1000 (e.g., controller 1002), to calibrate constituent laser diodes 1030, to couple other external compatible devices (e.g. another medical instrument 1000, a probe version of the medical instrument 1000, a computer device, a personal digital assistant (PDA)) and/or to perform diagnostics of the medical instrument 1000.

In one embodiment, the medical instrument 1000 may be powered by a lithium-ion rechargeable battery placed in an inside thereof. Here, the battery charger may plug into the medical instrument 1000 through the external connector 1008, and may closely monitor charge current as well as maximum allowed voltage. In one or more embodiments, the battery may be supplied with a safety circuitry to prevent over-charging/over-discharging of the battery. In one or more embodiments, constituent components of the medical instrument 1000 may be powered during charging of the battery, but user interaction with the medical instrument 1000 may not be possible.

In one or more embodiments, the controller 1002 may be interfaced with an external memory 1010 to enable the medical instrument 1000 to record data indicating a diagnostic requirement of the medical instrument 1000. In one or more embodiments, the recorded data may be useful in enabling servicing of the medical instrument 1000. For example, corrective diagnostics may be performed on the medical instrument 1000 by service personnel following a return of the medical instrument 1000 by a user. In one or more embodiments, the external memory 1010 may be a non-volatile memory such as an Electrically Erasable Programmable Read-Only Memory (EEPROM).

In one or more embodiments, the medical instrument 1000 may be provided with a user button 1014 (shown in FIG. 10 as turning on the controller 1002) to simplify operations thereof. In one embodiment, the user button 1014 may serve as both the power ON/OFF button and the mode selection button.

In one or more embodiments, the medical instrument 1000 may be provided with a speaker 1016 (shown in FIG. 10 as being controlled by the controller 1002) to generate audible alerts as well as indicate the pressing of the user button 1014. In one or more embodiments, the audible alerts may indicate one or more of an operational status of the medical instrument 1000, a beginning of a mode of operation, a beginning of a segment, an end of a mode of operation, and an end of the segment. In or embodiments, all audible alerts may be muted by the user during use of the medical instrument 1000.

In one or more embodiments, to enhance serviceability of the medical instrument 1000, a real-time clock 1018 (shown in FIG. 10 as being interfaced with the controller 1002) may be implemented in the medical instrument 1000. In one or more embodiments, data recorded in the external memory 1010 may always be tagged with a current date and time at the time of recording. In one or more embodiments, this may enable a history of use of the medical instrument 1000 to be tracked. For example, when a medical instrument 1000 is returned to the service personnel, the service personnel may be better equipped to understand problems associated with the functioning of the medical instrument 1000.

In one or more embodiments, the medical instrument 1000 may be equipped with one or more LEDs 1020 and a display 1022 (e.g., seven segment display) that serve as user indicators. In FIG. 10, the LEDs 1020 and the display 1022 are shown as being controlled by the controller 1002. In one embodiment, the operational state of the medical instrument 1000 may be indicated with an LED emitting green light that may turn red during a power down. Here, another LED may be provided to indicate battery state and battery charging. For example, if the light emitted by this LED turns yellow during normal operation, it may be indicative of a low power level of the battery. The battery may then need to be charged. The LED may emit red light in a blinking state until charging may be complete, following which the LED may continue to emit green light. In one or more embodiments, the display 1022 may indicate modes that are loaded onto the medical instrument 1000, and, in one embodiment, the modes may be indicated on the display as 0-9. Here, the user may select a mode using the mode selection feature of the user button 1014.

In one or more embodiments, one of the purposes of the controller 1002 may be to control the laser diodes 1030 through laser drivers 1026 thereof. In one or more embodiments, the controller 1002 may control the power level of the laser diodes 1030, and also the flashing of the laser diodes 1030. In addition, in one or more embodiments, the controller 1002 may monitor a light sensor 1024 that measures the ambient light outside the medical instrument 1000. This measurement may be used to control the light intensity of the user indicator LEDs 1020.

In one or more embodiments, the controller 1002 may have the ability to sense the operating current of each laser diode 1030 (see the current sensor 1028 in FIG. 10), which may be used to deactivate laser diodes 1030 that may have failed. In one or more embodiments, this may ensure safety of operation of the medical instrument 1000. In one or more embodiments, current may also be sensed during calibration of the medical instrument 1000 to ensure proper operation of the laser diodes 1030. In one or more embodiments, a power management circuitry of the laser diodes 1030 may be controlled by the controller 1002. In one or more embodiments, infrared light may also be emitted from the infrared LEDs 1040.

In one or more embodiments, the medical instrument 1000 may also include a number of infrared LEDs 1040 (shown as being controlled in FIG. 10 by the controller 1002) to emit infrared light during a duration of a mode of operation. In one or more embodiments, the infrared LEDs 1040 may operate in conjunction with one or more of the visible LEDs 1020.

In one or more embodiments, the controller 1002 may monitor a temperature sensor 1032 to obtain accurate values of the temperatures of the laser diodes 1030. In one or more embodiments, variations of temperature of the laser diodes 1030 may also be tracked.

In one or more embodiments, the medical instrument 1000 may include a reset controller 1006 to monitor a reset button.

For example, when a user depresses the reset button and holds the reset button for, say, 5 seconds, the reset controller 1006 may send a reset signal to the controller 1002 to reset the medical instrument 1000. Here, 5 seconds is the threshold time period, and if a user presses the reset button for a time period exceeding the threshold time period, the medical instrument 1000 may be reset.

In one or more embodiments, when the medical instrument 1000 is turned ON and is in an idle state, an LED 1020 indicating power may emit green light. In one or more embodiments, a shut off timer may be started internally to turn the medical instrument 1000 off in case of inactivity (e.g., no further pressing of buttons) for a time period exceeding another threshold time period.

In one or more embodiments, the medical instrument 1000 may be pre-programmed (e.g., by the manufacturer) with several operational modes. In one or more embodiments, the modes may be pre-programmed with the duration of treatment for a therapeutic condition, and the specific frequencies the medical instrument 1000 may be operating at.

Figure 11:
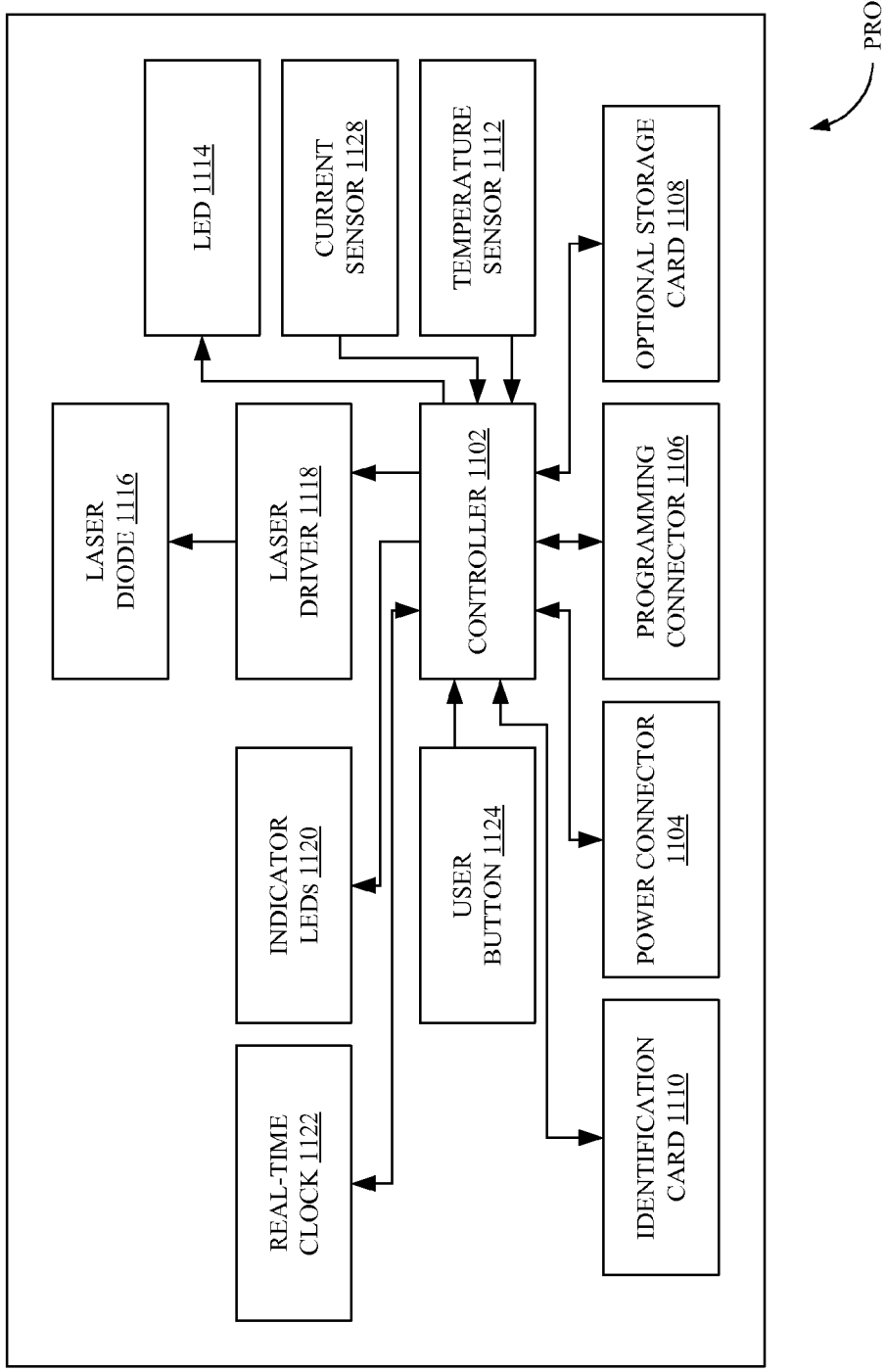
FIG. 11 is a schematic view of a probe device, according to one or more embodiments.

In one or more embodiments, where there is a requirement of directed, high-power dosage in a narrow region of a biological medium, the second medical instrument 200B, for example, may be a probe device (as illustrated in FIG. 11).

FIG. 11 is a schematic view of a probe device 1100, according to one or more embodiments. The probe device 1100 may be substantially similar to, or the same as, the medical instrument 200B. In one or more embodiments, the probe device 1100 may include a controller 1102 to control all components of the probe device 1100. In one or more embodiments, an operating program of the controller 1102 may be user-upgraded using an optional storage card 1108. In one or more embodiments, the optional storage card 1108 may be a flash card from which different programs may be read.

In one or more embodiments, the probe device 1100 includes a power connector 1104 through which a battery of the probe device 1100 may be charged. In one or more embodiments, the medical instrument 200A may be used to power the probe device 1100 through the power connector 1104. In one or more embodiments, the probe device 1100 may include an identification card 1110. The identification card 1110 may include information regarding types of treatment modes to be activated. The information on the identification card 1110 may be read by controller 1102.

In one or more embodiments, the probe device 1100 may include a programming connector 1106 through which a programming/calibration interface may be provided. In one or more embodiments, the probe device 1100 may be calibrated by a manufacturer and/or serviced by service personnel through the programming connector 1106. In one or more embodiments, a data processing system 412 may be coupled to the probe device 1100 through the programming connector 1106. In one or more embodiments, the programming connector 1106 may not be available to a user but only available to the manufacturer and/or service personnel.

In one or more embodiments, an integrated laser driver 1118 may control a laser diode 1116 of the probe device 1100. In one or more embodiments, an operating current of the laser diode 1116 and/or a light output of the laser diode 1116 may be monitored to maintain a constant output of the laser diode 1116. In one or more embodiments, the laser diode 1116 may be calibrated during the manufacturing process and/or the laser driver 1118 may be configured to handle a range of laser diodes.

In one or more embodiments, LEDs (1114, 1120) may be provided to indicate an operational state of the probe device 1100. A light from an LED 1114 may also indicate that the optional storage card 1108 is properly inserted and recognized. In another example, a number of LEDs 1120 may indicate modes selected and/or progress during boot-up. In one or more embodiments, a separate LED 1114 may indicate activity of the laser diode 1116.

In one or more embodiments, in order for corrective diagnostics to be performed by service personnel and/or operating statistics to be obtained by the manufacturer, a real-time clock 1122 may be provided in the probe device 1100. In one or more embodiments, the real-time clock 1122 may be programmed during manufacturing. In one embodiment, power to the real-time clock 1122 may be supplied by a coin cell battery of the probe device 1100.

In one or more embodiments, the controller 1102 may monitor the current of the laser diode 1116 during operation of the laser diode 1116 through a current sensor 1128. In one embodiment, the current data may be used in the calibration of the probe device 1100.

In one or more embodiments, a temperature sensor 1112 may be provided in the probe device 1100 to monitor a temperature of the laser diode 1116 in order to ensure safety of operation of the probe device 1100.

In one or more embodiments, when the probe device 1100 is powered up, green light may be emitted from an LED 1120. In one embodiment, when the optional storage card 1108 is not present, the green LED 1120 may start to blink to indicate the need to insert the optional storage card 1108. In one or more embodiments, upon insertion of the identification card 1110 and checking for updates residing in the identification card 1110, modes of operation may be downloaded into the probe device 1100. In one or more embodiments, modes of operation present on the identification card 1110 may be loaded.

In one or more embodiments, user selection of modes of operation may be accomplished through a user button 1124. In one or more embodiments, the probe device 1100 may be turned on by a user holding the user button 1124 for a time period exceeding a threshold time period of, say, 5 seconds. In one or more embodiments, a warning LED 1114 may be provided to indicate a state where a laser diode 1116 operating at a wavelength outside the visible spectrum may be used. In one or more embodiments, the probe device 1100 may also be turned off by a user depressing the user button 1124 for a time period exceeding another threshold time period.

In one or more embodiments, if at any point the identification card 1110 is removed, the laser diode 1116 may be turned off, and the probe device 1100 may return to a boot-up state thereof.

FIG. 12 is a system view illustrating mode server 1200 communicating information associated with a mode to a medical instrument(s) 200A-N through a client device(s) 1202A-N via a network 1204, according to one or more embodiments. Particularly, FIG. 12 illustrates the mode server 1200, the client device(s) 1202A-N, the network 1204, and the medical instrument(s) 200A-N, according to one or more embodiments. It should be noted that the medical instruments described herein the Figure are substantially similar or the same as illustrated in previous Figures. Also, the client device(s) 1202A-N described herein may be substantially similar or the same as illustrated in previous figures.

The mode server 1200 may provide different modes of operation for the medical instruments 200A-N via the network 1204. The client device 1202A-N may be any computing device (e.g., the data processing system 412) that can interface the medical instrument 200A-N for communicating the mode of operation to the other medical instrument 200A-N. The mode may control the laser diodes and the LED diodes (not shown in figures) to generate a laser wavelength based on the mode. In one or more embodiments, the mode may configure the laser diodes and the LED diodes to generate laser at different wavelengths. In one or more embodiments, the client device 1202A-N may include, but is not limited to, a computer. In one or more embodiments, the client device 1202A-N upon receiving the information may provide an acknowledgment to the mode server via the network 1204. In one or more embodiments, the information associated with the mode may include, but is not limited to, a mode configuration, setting information, and handling instructions. In one or more embodiments, the mode server 1200 may be supported by a custom mode database (not shown in the Figure). The custom mode database may be a central resource for information associated with the modes. In one or more embodiments, a custom mode of operation may be configured into the medical instrument 200A-N and the treatment based on the custom mode may be provided to the user. In one or more embodiments, the custom mode configured by the user may be communicated to the mode server 1200 through the client device 1202A-N via the network 1204.

Figure 13:
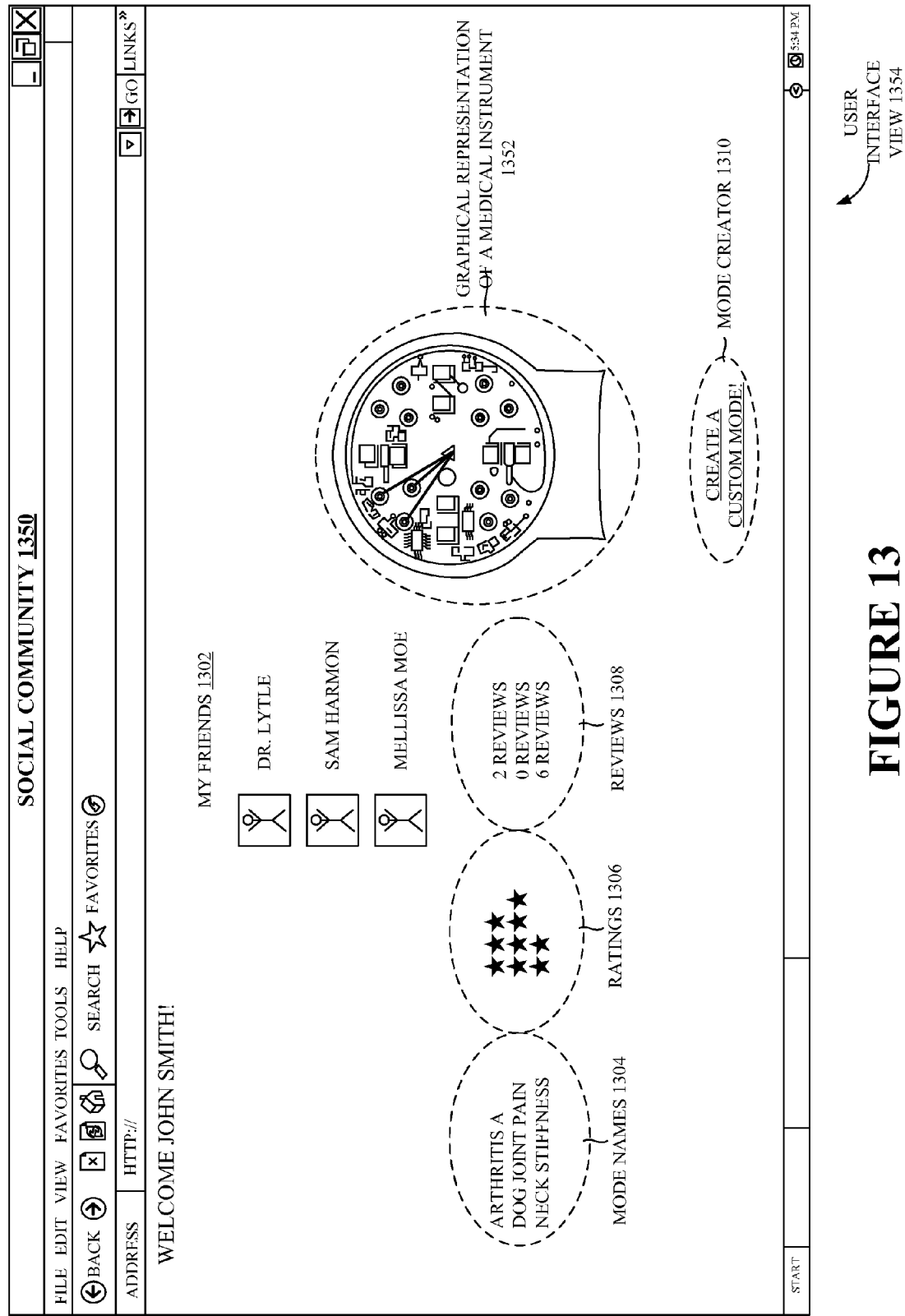
FIG. 13 is a user interface view providing a platform for medical instrument users to interact with other medical instrument users in an online social community environment, according to an example embodiment.

FIG. 13 is a user interface view 1354 providing a platform for medical instrument users to interact with other medical instrument users in an online social community environment 1350, according to an example embodiment. In one or more embodiments, the users of the medical instruments 200A-N may be provided with an online social community environment. The medical instrument users may communicate with other medical instrument users, doctors, etc., to share their experiences, provide suggestions, etc. An example embodiment illustrates a user page of the user John Smith. A list of my friends 1302 illustrates a list of friends of the user John Smith, who may be a part of social community 1350. In the example embodiment, the user John Smith may have Dr. Lytle, Sam Harmon, and Mellissa Moe as connections. The mode names 1304 may illustrate names of the modes of operation associated with the therapeutic conditions (e.g., type 1 or diabetes type 2). The ratings 1306 may provide information to other users regarding the opinion of the users associated with the mode of treatment. The reviews 1308 may illustrate the number of reviews performed by other users. In one or more embodiments, the user John Smith may review the modes and provide ratings to the associated modes.

A mode creator 1310 may be a link that enables the user of the user interface (e.g., John Smith) to create a custom mode or to upload a mode created by the user (e.g., John Smith). A graphical representation of the medical instrument 1352 may illustrate a type of medical instrument for which a custom mode can be created. In one or more embodiments, a different type of medical instrument may be illustrated for which the user wants to create a custom mode via functions provided in the user interface (e.g., through graphical buttons, clicks, etc.).

Figure 14:
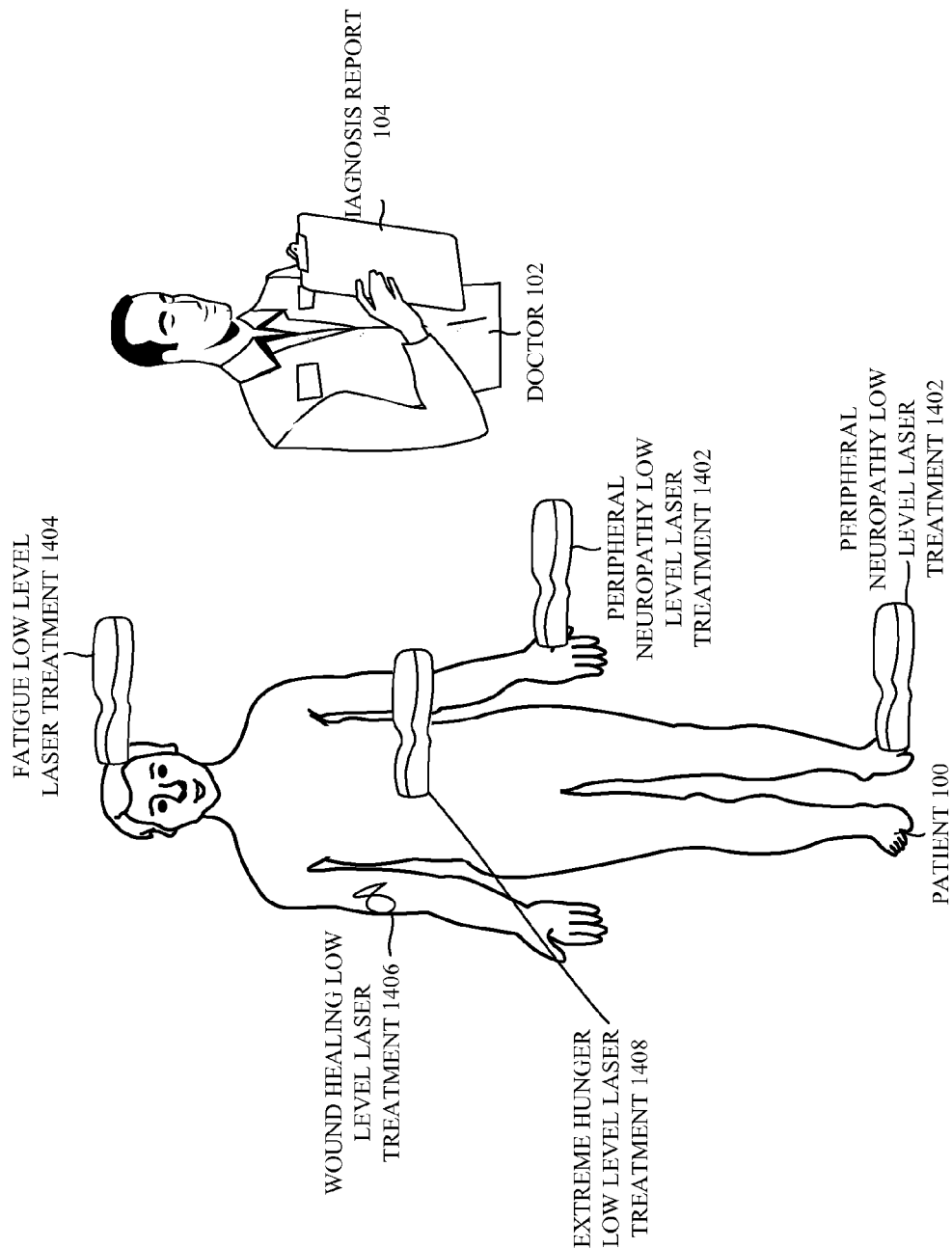
FIG. 14 is table showing the common symptoms exhibited by diabetic type 1 or type 2 patients.

FIG. 14 illustrates the low-level laser treatment of the patient 100 for wound healing 1406, peripheral neuropathy 1402 and extreme hunger 1408. These are some of the symptoms shown in table 1550 used for disease diagnosis in patient 100 who may be suffering from a diabetes type 1 or type 2 disease.

FIG. 15 is a tabular view 1550 diabetes type 1 (1502) and type 2 (1506) symptoms. Low-level laser treatment 1504 and 1508 for diabetes type 1 and type 2 are shown. The low-level laser treatment can have different treatment modes and different wavelengths of lasers for each symptom and may vary depending on the needs of the patient 100.

Although the present embodiments have been described with reference to specific example embodiments, it will be evident that various modifications and changes may be made to these embodiments without departing from the broader spirit and scope of the various embodiments. Accordingly, the specification and drawings are to be regarded in an illustrative manner rather than a restrictive sense.

What is claimed:

1. A method comprising:
generating a first soliton wave through a laser diode of a first medical instrument at a wavelength of approximately 660 nm to 808 nm;
generating a second soliton wave through a laser diode of a second medical instrument at a wavelength of approximately 660 nm to 808 nm;
applying the first soliton wave to a first application point located over the left kidney of a patient suffering from Type I or Type II diabetes on the small of the patient's back, one hand width above the belt and one hand width to the left of the spine, for a one minute duration;
repeating the application of the first soliton wave to the first application point for the one minute duration two more times in the same day;
applying the second soliton wave to a second application point located over the extreme outer edge of the patient's inner elbow crease, for a one minute duration;
repeating the application of the second soliton wave to the second application point for the one minute duration two more times in the same day;
coordinating the application of the first soliton wave and the second soliton wave through an algorithm that controls the generation of the first soliton wave of the first medical instrument and the generation of the second soliton wave of the second medical instrument; and
reducing a glycosylated hemoglobin A1c (HbA1c) of the patient as a result of the application of the first soliton wave and the second soliton wave.

2. The method of claim 1, further comprising:
adjusting at least one of a pulsation power, a pulsation frequency, and a pulsation duration of the first medical instrument and the second medical instrument through a controller of the first medical instrument and a controller of the second medical instrument, respectively.

3. The method of claim 1, further comprising:
authenticating the first medical instrument based on an identifier associated with the first medical instrument using a processor;
authenticating a user of the first medical instrument based on a password using the processor;
generating a graphical representation of the first medical instrument;
providing a set of rules associated with the first medical instrument based on the identifier associated with the first medical instrument and the user;
generating a first custom mode of operation of the first medical instrument based on a response of the user;
creating a name associated with the first custom mode of operation;
automatically programming the first medical instrument based on the first custom mode;
sharing the first custom mode with other users and other medical instruments based on the set of rules and a preference of the user;
authenticating the second medical instrument based on an identifier associated with the second medical instrument using the processor;
authenticating the user of the second medical instrument based on a password using the processor;

generating a graphical representation of the second medical instrument;
providing a set of rules associated with the second medical instrument based on the identifier associated with the second medical instrument and the user
generating a second custom mode of operation of the second medical instrument based on a response of the user;
creating a name associated with the second custom mode of operation;
automatically programming the second medical instrument based on the second custom mode;
sharing the second custom mode with other users and other medical instruments based on the set of rules and a preference of the user.

4. The method of claim 1, further comprising:
applying the first soliton wave and the second soliton wave every other day up to sixty days.

\* \* \* \* \*